(12) United States Patent
Reidt et al.

(10) Patent No.: US 9,162,259 B2
(45) Date of Patent: Oct. 20, 2015

(54) DEVICE AND METHOD FOR THE REGENERATION OF BIOSENSORS

(75) Inventors: Ulrich Reidt, Schwalmstadt (DE); Alois Friedberger, Oberpframmern (DE); Barbara Baur, Munich (DE); Martin Eickhoff, Giessen-Allendorf (DE); Tom Lueders, Munich (DE); Gerhard Mueller, Grafing (DE)

(73) Assignee: EADS Deutschland GmbH, Ottobrunn (DE)

( * ) Notice: Subject to any disclaimer, the term of this patent is extended or adjusted under 35 U.S.C. 154(b) by 0 days.

(21) Appl. No.: 12/678,608

(22) PCT Filed: Sep. 12, 2008

(86) PCT No.: PCT/EP2008/007572
§ 371 (c)(1),
(2), (4) Date: Mar. 17, 2010

(87) PCT Pub. No.: WO2009/036931
PCT Pub. Date: Mar. 26, 2009

(65) Prior Publication Data
US 2011/0139189 A1   Jun. 16, 2011

(30) Foreign Application Priority Data
Sep. 18, 2007   (DE) .................. 10 2007 044 708

(51) Int. Cl.
*B08B 3/04* (2006.01)
*B08B 3/12* (2006.01)
(Continued)

(52) U.S. Cl.
CPC . *B08B 3/04* (2013.01); *B01L 99/00* (2013.01); *B08B 3/12* (2013.01); *B01L 2300/0636* (2013.01); *G01N 2035/00277* (2013.01)

(58) Field of Classification Search
CPC ... B01L 2300/0636; B01L 99/00; B08B 3/04; B08B 3/12; B82Y 15/00; G01N 2035/00277
USPC ................. 134/34, 42, 184, 198; 204/402
See application file for complete search history.

(56) References Cited

U.S. PATENT DOCUMENTS 5,624,537 A * 4/1997 Turner et al. ............ 422/82.01
5,777,372 A * 7/1998 Kobashi .................... 257/414
(Continued)

FOREIGN PATENT DOCUMENTS

DE    35 14 668 C2   7/1987
DE    100 22 398 B4  3/2011
(Continued)

OTHER PUBLICATIONS

Myszka et al., "Kinetic analysis of a protein antigen-antibody interaction limited by mass transport on an optical biosensor," Biophysical Chemistry 64 (1997), pp. 127-137.*
(Continued)

*Primary Examiner* — Michael Kornakov
*Assistant Examiner* — Douglas Lee
(74) *Attorney, Agent, or Firm* — Crowell & Moring LLP

(57) ABSTRACT

A device for the regeneration of a biosensor having an immobilized and biologically active material applied to the surface of a carrier that is suitable for interacting with a substance to be analyzed. The device comprises at least one injector through which, by means of a pump, at least one solution can be applied to the surface of the carrier for the purposes of rinsing the biologically active material.

6 Claims, 1 Drawing Sheet

(51) Int. Cl.
*B01L 99/00* (2010.01)
*G01N 35/00* (2006.01)

(56) References Cited

U.S. PATENT DOCUMENTS

| | | | |
|---|---|---|---|
| 6,582,926 B1* | 6/2003 | Chilkoti | 435/7.1 |
| 6,914,279 B2* | 7/2005 | Lu et al. | 506/39 |
| 2002/0011276 A1 | 1/2002 | Sander | |
| 2002/0074513 A1* | 6/2002 | Abel et al. | 250/458.1 |
| 2003/0100127 A1 | 5/2003 | Corn et al. | |
| 2004/0009500 A1 | 1/2004 | Benters et al. | |
| 2004/0071888 A1 | 4/2004 | Chondroudis et al. | |
| 2005/0130226 A1 | 6/2005 | Ahn et al. | |
| 2005/0268943 A1 | 12/2005 | Schleifer | |
| 2006/0275893 A1 | 12/2006 | Ishii et al. | |
| 2007/0099189 A1 | 5/2007 | Gomez-Elvira Rodriguez et al. | |

FOREIGN PATENT DOCUMENTS

| | | |
|---|---|---|
| JP | 2002-365288 | 12/2002 |
| JP | 2005-172637 | 6/2005 |
| JP | 2005-237378 A | 9/2005 |
| JP | 2006-003349 | 1/2006 |
| WO | WO 01/79535 A2 | 10/2001 |
| WO | WO 02/01196 A1 | 1/2002 |
| WO | WO 02/061428 A2 | 8/2002 |

OTHER PUBLICATIONS

Naimushin, A. et al., "Airborne analyte detection with an aircraft-adapted surface Plasmon resonance sensor system," Sensors and Actuators B, vol. 104, No. 2 (Jan. 2005), pp. 237-248.*

Brynda, E., "Chapter 18: Methods for Attachment of Antibodies onto Optical Biosensors", Optical Chemical Sensors (2006), pp. 387-401.*

Brynda, E. "Chapter 18: Methods for Attachment of Antibodies onto Optical Biosensors", Optical Chemical Sensors (2006), pp. 387-401.*

Naimushin, A. et al. "Airborne analyte detection with an aircraft-adapted surface Plasmon resonance sensor system," Sensors and Actuators B, vol. 104, No. 2 (Jan. 2005), pp. 237-248.*

Corresponding International Search Report dated Jan. 23, 2009 w/ English Translation (Six (6) pages).

Naimushin, Alexei N. et al., "Airborne Analyte Detection with an Aircraft-Adapted Surface Plasmon Resonance Sensor System", Sensors and Actuators B, 2005, pp. 237-248, vol. 104, Elsevier B.V.

Yu, Quiming et al, "Detection of Low-Molecular-Weight Domoic Acid Using Surface Plasmon Resonance Sensor", Sensors and Actuators B, 2005, pp. 193-201, vol. 107, Elsevier B.V.

Schlensog, Marc D. et al., "A Love-Wave Biosensor Using Nucleic Acids as Ligands", Sensors and Actuators B, 2004, pp. 308-315, vol. 101, Elsevier B.V.

* cited by examiner

DEVICE AND METHOD FOR THE REGENERATION OF BIOSENSORS

BACKGROUND OF THE INVENTION

This application is a national stage of PCT International Application No. PCT/EP2008/007572, filed Sep. 12, 2008, and claims priority under 35 U.S.C. §119 to German Patent Application No. 10 2007 044 708.8, filed Sep. 18, 2007, the entire disclosures of which are herein expressly incorporated by reference.

The invention relates to a device for the regeneration of a biosensor that includes, on the surface of a carrier, an immobilized and biologically active material designed to interact with a substance to be analyzed.

Biosensors relevant in the context of the present invention are equipped with biological components. The operating principle of a biosensor is based on direct spatial coupling of an immobilized biologically active material located on the surface of a sensor element with an electronic, optical or other transducer, and an electronic amplifier. Such biological materials can be, for example, antibodies, enzymes, organelles, microorganisms or nucleic acids.

The immobilized biological material located on the surface of the sensor interacts with the substance to be analyzed. The interaction may consist of, for example, an interaction between enzyme and substrate, or between an antibody and an antigen, which results in physical alterations, for example of the coating thickness, the refractivity, the absorption of light, the electrical charge or the ion concentration (e.g. change of pH-value) of specific ions in the area of the respective surface. These changes can be measured by measuring devices like optical sensors, amperometric electrodes or field-effect transistors operating based on potentiometric methods.

However, after the measuring procedure, the initial state of the system must be restored. Accordingly, the measurement of the substance to be analyzed with the biosensor is performed in three steps: First, there is the biochemical reaction of the substance to be analyzed by the biological system of the biosensor, after which the reaction is converted into an electric or optical signal, and the signal is then processed and amplified. Consequently, the selectivity and sensitivity of a biosensor is derived from the biological system that is used.

The biological material is arranged on the biosensor by means of a carrier, onto which the material is applied, or on which the material is embedded between two membranes. The biological material can also be immobilized directly on the carrier after the chemical functionalization of the carrier. Furthermore, the biological system can be applied onto a membrane that afterwards is connected with the surface of the transducer. Applications suitable for biosensors in the analysis of water and sewage can be divided into biosensors for the analysis of single components, for the analysis of toxicity and mutagenicity, and for the analysis of the biochemical oxygen demand (BOD). Examples include the measurement of a glucose concentration in the blood of a human being (for example, following an operation). The glucose concentration could be analyzed as the change of the pH-value or as a change of the oxygen concentration as the consequence of glucose-oxidase catalyzed glucose oxidation.

A further biosensor is known for the measurement of the penicillin concentration in a bioreactor (fermenter), in which bacteria strains are cultured that express and secrete penicillin into the culture medium. When the concentration is sufficiently high, the substance can be extracted from the culture medium by organic solvents and after several precipitation reactions. The biological component of the sensor used in this context is the enzyme acylase. The penicillin-cleaving enzyme is embedded in a membrane on which a pH-electrode is located. Once the penicillin concentration in the medium increases, the enzyme catalyzes the formation of increasing amounts of phenyl-acetic acid, and thereby changes the pH-value in the vicinity of the electrode. Hence, it is possible to determine the penicillin concentration based on the pH-value.

Further applications of biosensors concern the analysis of bacteria content in bathwater or sewage. It is possible to apply antibodies directed against certain kinds of bacteria on an oscillating membrane. When the respective bacteria float by the sensor, they attach to the antibodies, thereby diminishing the oscillation of the membrane. A corresponding signal is provided once the oscillation of the membrane falls below a certain value.

DESCRIPTION OF THE INVENTION

The surface of the biosensor can consist of, for example, gallium nitride (GaN) or another optically transparent semiconductor (SC). Gallium nitride is an optically transparent semiconductor that can be grown epitaxially on sapphire substrates that are likewise optically transparent. This property can be used for the excitation of a fluorescent dye labeled with a mobile antibody by means of a light source positioned on the backside of the surface. This mobile antibody binds to an antigen that at the same time is bound to an unlabeled immobilized antibody. This type of antigen-antibody binding thereby follows the principle of a sandwich-ELISA. The fluorescent light emitted by the mobile antibody can be captured with a sensitive detector after the recognition of the antigen. An immobilization of antibodies on the surface of the semiconductor or on other materials such as for example ZnO, $SnO_2$ or diamond can be achieved by various methods, for example, by crosslinking with glutaraldehyde or bromocyanide (BrCN).

Immobilization of antibodies on the sensor surface can also be achieved by protein-protein interaction with protein G and protein A, the protein G consisting of *Staphylococcus aureus*. As an alternative to protein G, protein A can be used. Selecting between the use of protein G or protein A as a possibility for immobilization frequently depends on the derivation of the antibodies (i.e., on the particular organism the antibody was raised in). Both methods can be applied in combination with adequate crosslinkers. In this case, the respective protein A or G is immobilized on the surface of the sensor with glutaraldehyde. After crosslinking, the actual application of the antibody takes place via a protein-protein interaction at the $F_c$-domain of the antibody. The advantage of this method is an optimal utilization of the antibodies on the surface of the sensor. The bacterium *Escherichia Coli* (*E. coli*) can serve as an example of an antigen.

One disadvantage of such biosensors lies in their short lifespan and low biological stability. In this regard, it must be considered that a denaturation of the immobilized protein- and nucleic acid components takes place on the surface of the sensor, so that a degradation of immobilized macromolecules such as nucleic acids and proteins can be considered as a drawback of such biosensors. Thus, it is necessary to improve the lifespan and the stability of such immobilized biologically active materials.

Therefore, it is an object of the present invention to overcome the above-mentioned disadvantages of the state of the art by providing a device and a method for the regeneration of biosensors.

This and other objects and advantages are achieved by the method and apparatus according to the invention, for the automatic removal of biological components such as antibodies or enzymes. In this process, special solutions that remove used biological material such as antibodies, enzymes, nucleic acids and other residues can be pumped over the sensor surface by means of an automatic microfluid system. Once the sensor surface has been rinsed, the immobilization process is repeated.

The device according to the invention has at least one injector through which at least one solution can be directed onto the surface of the carrier by a pump in order to rinse the biologically active material. Advantageously, the device has a valve location, by which different solutions can be optionally applied to the surface of the carrier via the injector and the pump. The biologically active material of the biosensor includes antibodies, enzymes, organelles, microorganisms, proteins or nucleic acids. Furthermore, the biosensor has a transducer that produces a signal that can be amplified with an amplifier and can be submitted to an evaluation system.

Advantageously, the application of the at least one solution on the biologically active material by the injector is in form of a microfluid system, which can be integrated into the biological sensor, so that it forms together with the sensor, a device according to the present invention. The valve system can be operable manually or automatically, so that depending on the applicable requirement, different solutions can be applied on the surface of the carrier. To achieve a longer lifespan, the reagents can be refrigerated during storage.

The carrier of the biosensor can, for example, consist of a semiconductor in the form of a gallium nitride- a zinc oxide- or a diamond coating that is applied onto a carrier material. The system is not limited to a single injector; rather, several injectors can be used simultaneously in order to rinse the surface of the carrier.

Furthermore, the present invention concerns a process for the regeneration of a biosensor using the device as described above. All purification steps, as well as all steps for the immobilization of the surface of the carrier, can be performed by means of an automated fluid system. The main components of the automated system include the valves, which can be adapted to the different solutions. Moreover, the system includes pumps, which aspirate the different solutions via the valves and directs them to the surface of the sensor via injectors. The present system may include either one each of a valve, pump and injector, or a plurality thereof. Consequently, there is not only the possibility to clean the surface of the biosensor from the previously used biologically active material, but the biologically active material on the surface of the carrier can even be regenerated and/or exchanged by means of the rinsing. The process of purification and of renewed immobilization may be supported by temperature-controlled fluids and/or sensor components, as well as through a coupling with ultrasound.

A further advantage of the presently disclosed automated biosensor regeneration is the exchange of, for example, the enzymatic properties or the nucleic acid. To this end, the enzyme is detached from the surface of the sensor by means of the solution and exchanged for another enzyme. This exchange is performed by choosing a different solution by means of the valve location. To this end, the transducer simply has to be suited for different enzymes. Furthermore, the regenerated biosensor must show a reproducible, calibratable and preferably linear performance according to the specific conditions of immobilization.

According to a further embodiment of the invention, the antibodies on the surface of the carrier are removed by the release of protein-protein interactions. The immobilization of protein A or G is known from affinity chromatography. Usually, the proteins are coupled to a polymer matrix like sepharose and are then used for the purification of antibodies. The coupling of protein G to gallium nitride, semiconductor surfaces or other surfaces thereby offers the advantage of regeneration according to the present invention. The subsequent protein-protein interaction via the $F_c$-domain (antibody fragment) of the antibody with the protein G that is immobilized on the surface of the semiconductor offers a further advantage.

Moreover, there is the possibility to automatically remove the antibodies by releasing the protein-protein interaction with the protein G. It is advantageous to release the bound antibody because of the protein-protein interaction between the $F_c$-domain of the antibody and the protein G. To this end, the expressed and purified $F_c$-domain of the antibody is applied to the biosensor in excess. The purified $F_c$-domain displaces the antibody from the surface and binds to the protein G in place of the antibody. When new antibody, at a high concentration, is added to the protein complex, protein G and $F_c$-domain, the antibody in turn replaces the $F_c$-domain on protein G so that the biosensor can be again available for use in measurements. This regeneration as well can be performed in an automated fluid system, the regeneration of the biosensor being substantially accelerated in this case.

Advantageously, the biologically active materials that are to be removed and to be immobilized again on the surface of the carrier are provided by the solutions, and the rinsing process is automated.

Using the appropriate reagents, the surface of the biosensor can be completely cleansed from molecules, so that also the protein G can be removed. Subsequently, these molecules as well are immobilized again.

A further embodiment is the immobilization of nucleic acids. Accordingly, single-stranded nucleic acids are applied to the sensor surface, for example on a semiconductor, and a complementary nucleic acid that is to be detected can be bound by hybridization. The complementary nucleic acid is bound by hydrogen-bonds between the nucleic acid base pairs. The nucleic acid can be then bound to, i.e. labeled with, a biological, chemical or physical substance. Based on this labeled nucleic acid, the actual signal can be detected in the biosensor. For regeneration of the biosensor, the entire nucleic acid can be displaced chemically or thermally by another complementary nucleic acid.

Moreover, it is possible to immobilize histidine-tagged enzymes by interaction with coupled nickel-nitrilotriacetic acid (Ni-NTA) or with another metal chelate. Enzymes can be produced recombinantly with a histidine tag (HIS-tag). These so-called HIS-tag enzymes bind selectively to nickel ions ($Ni^{2+}$) or to other metal ions with the additional histidines. In biochemistry, this property is used for enzyme purification. To this end, the HIS-tag enzyme is bound via nickel-nitrilotriacetic acid (Ni-NTA) or via another metal chelate and is removed again after several washing steps using imidazole or EDTA.

Moreover, through immobilization of Ni-NTA or of another metal chelate-ligand on a semiconductor it is on the one hand possible to efficiently bind an enzyme, on the other hand, the enzyme can be removed easily and can be exchanged for another enzyme. The removal and exchange between enzymes is carried out using the automated fluid system.

Other objects, advantages and novel features of the present invention will become apparent from the following detailed

DETAILED DESCRIPTION OF THE DRAWINGS

Figure 1:
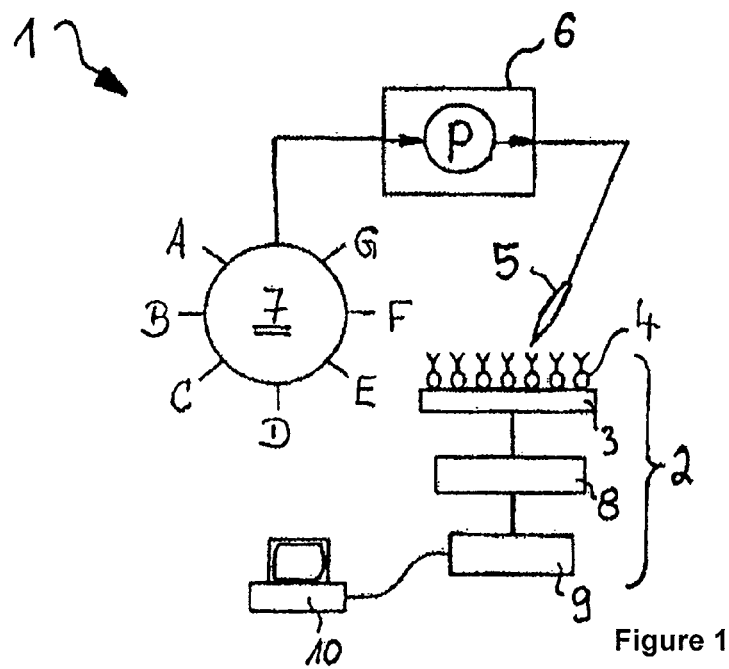
FIG. 1 is a schematic depiction of a device for regenerating a biosensor, by which different solutions (A-G) can be applied on the surface of a biosensor carrier through a valve location.

FIG. 1 shows the setup of a device 1 for regeneration of a biosensor 2. The biosensor comprises a carrier 3, on whose surface an immobilized biologically active material 4 has been applied. The biosensor 2 is displayed by its main components that comprise the carrier 3, the transducer 8, the amplifier 9 and an analysis system 10. The biologically active material 4 on the surface of the carrier 3 is shown in an enlarged format for the purposes of better illustration.

Device 1 features an injector 5, through which (via a pump 6) optionally one of the solutions A-G can be applied on the surface of the carrier 3. The choice of the different solutions A-G is made by a valve location 7, which can be operated either automatically or manually. The solutions A-G are stored in their respective containers, the solutions each comprising different biologically active materials. The illustration of injector 5 on top of the surface of the carrier 3 for the rinsing of biological material is provided only schematically; the system can also be a microfluid system integrated in the carrier 3 or at least in the cover of biosensor 2.

Figure 2:
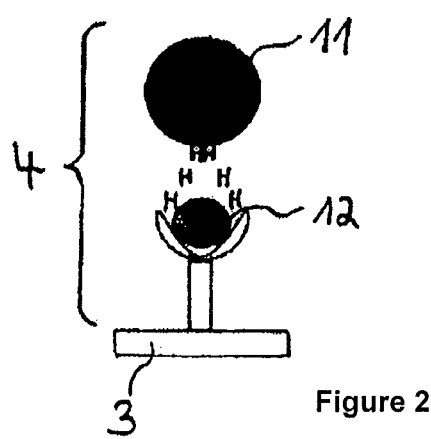
FIG. 2 depicts schematically the binding of an enzyme with an HIS-tag on the sensor surface via nickel-nitrilotriacetic acid (NiNTA)

FIG. 2 shows a schematic binding of an enzyme with HIS-tag on a sensor surface via nickel-nitrilotriacetic acid (Ni-NTA). Here, the HIS-tag enzyme is bound via immobilized nitrilotriacetic acid (Ni-NTA) or another metal chelate and is detached again after several washing steps with imidazole or EDTA. The enzyme 11 is displayed schematically on top of the nickel ion ($Ni^{2+}$) with the reference numeral 12, wherein the binding of the G-histidine-tag is indicated by a plurality of H-symbols. The enzyme 11 and the biologically active material 4 on the surface of the carrier 3 and the nickel ion 12 form the binding component of the molecule complex.

Figure 3:
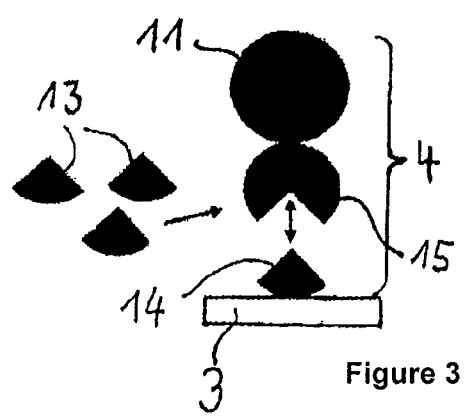
FIG. 3 depicts schematically the binding of a GST-fusion enzyme via the coupling of a substrate on a sensor surface.

In FIG. 3, the binding of a GST (glutathione-S-transferase)-fusion enzyme via the coupling of a substrate (reduced glutathione) on the surface of the sensor is shown. The biologically active material 4 is formed by the enzyme 11, the GST-tag 15 that is covalently bound to enzyme 11 with a peptide binding and by the free substrates 13 and the bound substrate 14 that is immobilized as GST-substrate. The free substrates 13 serve for the detachment of the GST-tag from the surface of the carrier 3.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

Legend
1 Device
2 Biosensor
3 Carrier
4 Biologically active material
5 Injector
6 Pump
7 Valve location
8 Transducer
9 Amplifier
10 Analysis system
11 Enzyme
12 $Ni^{2+}$
13 Free substrate
14 Immobilized GST substrate
15 GST Tag
A-G Solutions

The invention claimed is:

1. A fluorescent excitation biosensor having a light source that is positioned on the backside of a surface, comprising an immobilized and biologically active material that is applied to the surface of a carrier and is suited to interact with a substance to be analyzed, wherein the surface of the carrier is an optically transparent semiconductor in form of a gallium nitride-, a zinc oxide- or a diamond coating, or a composition including these materials, epitaxially grown on a sapphire substance; the biosensor further including a regenerating device comprising:
  at least two solution containers each containing different solutions, wherein at least one solution is a molecular-removal solution and at least one solution is a biologically active material; and
  an automated microfluid system integrated into the biosensor comprising:
  at least one injector through which, via a pump, at least one of the solutions is applied onto the surface of the carrier for rinsing the biologically active material; further comprising a valve arrangement, though which the solutions are applied successively by the injector and the pump to the surface of the carrier; and
  wherein the reagents and/or the carrier are temperature-controlled; and/or
  wherein a chamber with the carrier can be subjected to ultrasound.

2. The biosensor according to claim 1,
  wherein the biologically active material of the biosensor comprises one of antibodies, enzymes, organelles, microorganisms, proteins or nucleic acids.

3. The biosensor according to claim 1,
  wherein the biosensor has a transducer, which releases a signal that is amplifiable by an amplifier (9) and is delivered to an analysis system.

4. A method for the regeneration of a biosensor using a device according to claim 1,
  wherein the biologically active material on the surface of the carrier is exchanged by rinsing the surface of the carrier, wherein the specific binding properties of the biologically active material are exchanged, by removing the biologically active material present from the surface of the carrier, and
  applying afterwards a different biologically active material, wherein antibodies or enzymes on the surface of the carrier are removed manually or in an automated manner by removing protein-protein interactions by applying the purified Fc-domain as a part of the antibodies or enzymes to the biosensor in excess, and
  wherein the process of purification and of renewed immobilization is supported by temperature controlled fluids and/or sensor components and/or through coupling with ultrasound.

5. The method according to claim 4,
wherein biologically active material including nucleic acids, coenzymes, substrates or other macromolecules on the surface of a carrier are removed manually or in an automated manner by removing physical or chemical bonds.

6. The method according to claim 4,
wherein the biologically active materials to be removed and to be re-immobilized on the surface of the carrier are removed and re-immobilized by applying the solutions, and that the rinsing step is automated.

\* \* \* \* \*